US008118750B2

(12) United States Patent
Gerber

(10) Patent No.: US 8,118,750 B2
(45) Date of Patent: Feb. 21, 2012

(54) FLOW SENSORS FOR PENILE TUMESCENCE

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1675 days.

(21) Appl. No.: 11/255,533

(22) Filed: Oct. 21, 2005

(65) Prior Publication Data

US 2007/0092862 A1    Apr. 26, 2007

(51) Int. Cl.
A61B 5/103 (2006.01)

(52) U.S. Cl. ...................................................... 600/504

(58) Field of Classification Search ............. 607/39, 607/116, 118, 138, 143
See application file for complete search history.

(56) References Cited

U.S. PATENT DOCUMENTS

| | | | |
|---|---|---|---|
| 3,455,301 A * | 7/1969 | Clark ........................ 600/41 |
| 4,515,166 A | 5/1985 | Timm |
| 4,612,937 A * | 9/1986 | Miller ........................ 600/441 |
| 4,829,990 A | 5/1989 | Thuroff et al. |
| 4,848,361 A | 7/1989 | Penney et al. |
| 4,958,630 A | 9/1990 | Rosenbluth et al. |
| 5,372,133 A * | 12/1994 | Hogen Esch ................ 600/377 |
| 5,692,520 A | 12/1997 | Lavoisier |
| 5,931,783 A | 8/1999 | Redano |
| 5,947,901 A | 9/1999 | Redano |
| 6,015,393 A | 1/2000 | Hovland et al. |
| 6,063,034 A * | 5/2000 | Doten et al. ................ 600/448 |
| 6,162,188 A | 12/2000 | Barnea |
| 6,169,914 B1 | 1/2001 | Hovland et al. |
| 6,251,076 B1 | 6/2001 | Hovland et al. |
| 6,319,237 B1 | 11/2001 | Krumme |
| 6,464,653 B1 | 10/2002 | Hovland et al. |
| 6,650,943 B1 * | 11/2003 | Whitehurst et al. ........... 607/39 |
| 6,862,479 B1 | 3/2005 | Whitehurst et al. |
| 6,885,895 B1 | 4/2005 | Whitehurst et al. |
| 2002/0120219 A1 | 8/2002 | Hovland et al. |
| 2003/0125605 A1 | 7/2003 | Forsell |
| 2003/0125768 A1 | 7/2003 | Peter |
| 2003/0135090 A1 | 7/2003 | Forsell |
| 2003/0236557 A1 | 12/2003 | Whitehurst et al. |
| 2004/0015205 A1 | 1/2004 | Whitehurst et al. |
| 2005/0060005 A1 | 3/2005 | Boggs, II et al. |

FOREIGN PATENT DOCUMENTS

WO    WO 01/12065 A1    2/2001

OTHER PUBLICATIONS

U.S. Appl. No. 10/441,784, to Martin T. Gerber, filed May 19, 2003 entitled "Treatment of Sexual Dysfunction by Neurostimulation."

* cited by examiner

Primary Examiner — Carl H Layno
Assistant Examiner — Allen Porter, Jr.
(74) Attorney, Agent, or Firm — Shumaker & Sieffert, P.A.

(57) ABSTRACT

The disclosure describes blood flow sensors for detecting penile tumescence. A system according to the invention may include at least one sensor for sensing blood flow into the penis, and one sensor for sensing blood flow away from the penis. Detecting penile tumescence may be accomplished by comparing the flow of blood into the penis to the blood flow out of the penis. A greater inflow of blood indicates an increasing tumescence whereas a greater outflow of blood indicates a decreasing tumescence. The sensors may be used for short- or long-term monitoring of penile tumescence, or as closed-loop feedback in a therapeutic penile tumescence control system, which may deliver electrical or chemical stimulation therapy to control a tumescence or erectile state, thus treating sexual dysfunction or, more specifically, erectile dysfunction.

58 Claims, 8 Drawing Sheets

FLOW SENSORS FOR PENILE TUMESCENCE

TECHNICAL FIELD

The invention relates to implantable medical devices and, more particularly, implantable sensors.

BACKGROUND

Sexual dysfunction is a common problem afflicting men and women of all ages, genders, and races. Erectile dysfunction is a serious condition for many males, and it may include a variety of problems. Some of these problems include the inability to create an erection, incomplete erections and brief erectile periods. Sexual dysfunction in females may also affect the performance of erectile tissues, such as clitoris. These conditions may be associated with nervous system disorders, and may be caused by aging, injury, or illness.

In some cases, erectile dysfunction can be attributed to improper nerve activity that incompletely stimulates the penis or female erectile tissue. For example, stimulation from the brain during arousal and sexual activity is responsible for activating erectile tissue. With respect to erectile disorders, the problem may be a lack of sufficient stimulation from the brain, or a break in communication of the stimulation. Erectile disorders may additionally or alternatively involve dysfunctional parasympathetic function that can be attributed to many factors including illness or injury.

Methods for treating erectile dysfunction include pharmaceutical treatment and electrical stimulation. Delivery of electrical stimulation to nerves running through the pelvic floor may provide an effective therapy for many patients. For example, an implantable neurostimulator may be provided to deliver electrical stimulation to the pudendal or cavernous nerves to activate erectile tissue, e.g., induce an erection in males.

SUMMARY

The disclosure is directed to blood flow sensors for detecting penile tumescence. A system according to the invention may include at least one sensor for sensing blood flow into the penis, and one sensor for sensing blood flow away from the penis. In some embodiments, detecting penile tumescence may be accomplished by comparing the flow of blood into the penis to the blood flow out of the penis. A greater inflow of blood indicates an increasing tumescence whereas a greater outflow of blood indicates a decreasing tumescence.

The sensors may be used for short- or long-term monitoring of penile tumescence, or as closed-loop feedback in a therapeutic penile tumescence control system. A therapeutic penile tumescence control system may deliver electrical stimulation and/or one or more therapeutic substances, e.g., drugs, to control a tumescence or erectile state, thus treating sexual dysfunction or, more specifically, erectile dysfunction. Electrical stimulation may be delivered to nerve structures associated with the erectile tissue, e.g., pelvic floor nerves such as the prostate parasympathetic nerves, cavernous nerves, pudendal nerves or sacral nerves. Therapeutic substances may also be delivered to such nerves, or to the erectile tissue. Such systems may include an implantable medical device to deliver the therapy. In some embodiments, the output of the sensors may be used to control delivery of venous outflow restriction therapy, which may be provided by a variety of types of venous outflow restriction, and may promote tumescence of erectile tissue.

The flow sensors may be implanted in or near the erectile tissue of either a male or female, e.g., in or near the penis of female sexual organs. In systems that include an implantable medical device, the sensors may be coupled to the implantable medical device wirelessly or via leads to transmit signals indicative of the arterial and venous flow. Systems according to the invention may also include an external programmer.

An external programmer may be wirelessly connected to the sensors and/or an implantable medical device. In embodiments that include an implantable medical device that delivers therapy, the patient may use the external programmer to control delivery of therapy, e.g., initiation and termination of therapy, by the implantable medical device. The external programmer may also control therapy independent of patient input based on tumescence information received from the sensors. In some embodiments, one or more of the sensors, implantable medical device, or external programmer stores tumescence information based on the flows detected by the sensors for short- or long-term monitoring of tumescence. Some embodiments may provide monitoring without delivery of therapy and, therefore, need not include a therapy-delivering implantable medical device.

Inadequate tumescence during sexual arousal, e.g., erectile dysfunction, may be a result of faulty nervous system function of the sexual organs. One or more flow sensors may provide short- or long-term monitoring of penile tumescence for storage and offline analysis by a clinician. In addition, flow sensors may provide feedback in a closed-loop therapy system to control and sustain an engorged state of erectile tissue during the course of sexual activity.

In one embodiment, the invention provides a method comprising detecting an arterial blood flow to an erectile tissue with a first sensor, detecting a venous blood flow away from the erectile tissue with a second sensor, and generating tumescence information that reflects the degree of tumescence of the erectile tissue based on the detected arterial and venous blood flows.

In another embodiment, the invention provides a system comprising a first sensor that detects arterial flow to an erectile tissue, a second sensor that detects venous flow away from the erectile tissue, and a processor that generates tumescence information that reflects the degree of tumescence of the erectile tissue based upon the detected arterial and venous blood flows.

In an additional embodiment, the invention provides a system comprising means for detecting an arterial blood flow to an erectile tissue, means for detecting a venous blood flow away from the erectile tissue, and means for generating tumescence information that reflects the degree of tumescence of the erectile tissue based upon the detected arterial and venous blood flows.

In various embodiments, the invention may provide one or more advantages. For example, implanting flow sensors to measure blood flow to and from a penis permits accurate tumescence information that can be saved for review, or used in real-time to provide closed-loop feedback therapy. Tumescence may be sensed without significantly obstructing or altering the physiological function or the sexual organs. In some embodiments, small flow sensors may also be placed adjacent to major blood vessels to and from the penis with minimally invasive surgical procedures. Once implanted near the base of the penis, the devices may avoid obstructing or hindering normal sexual activity.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
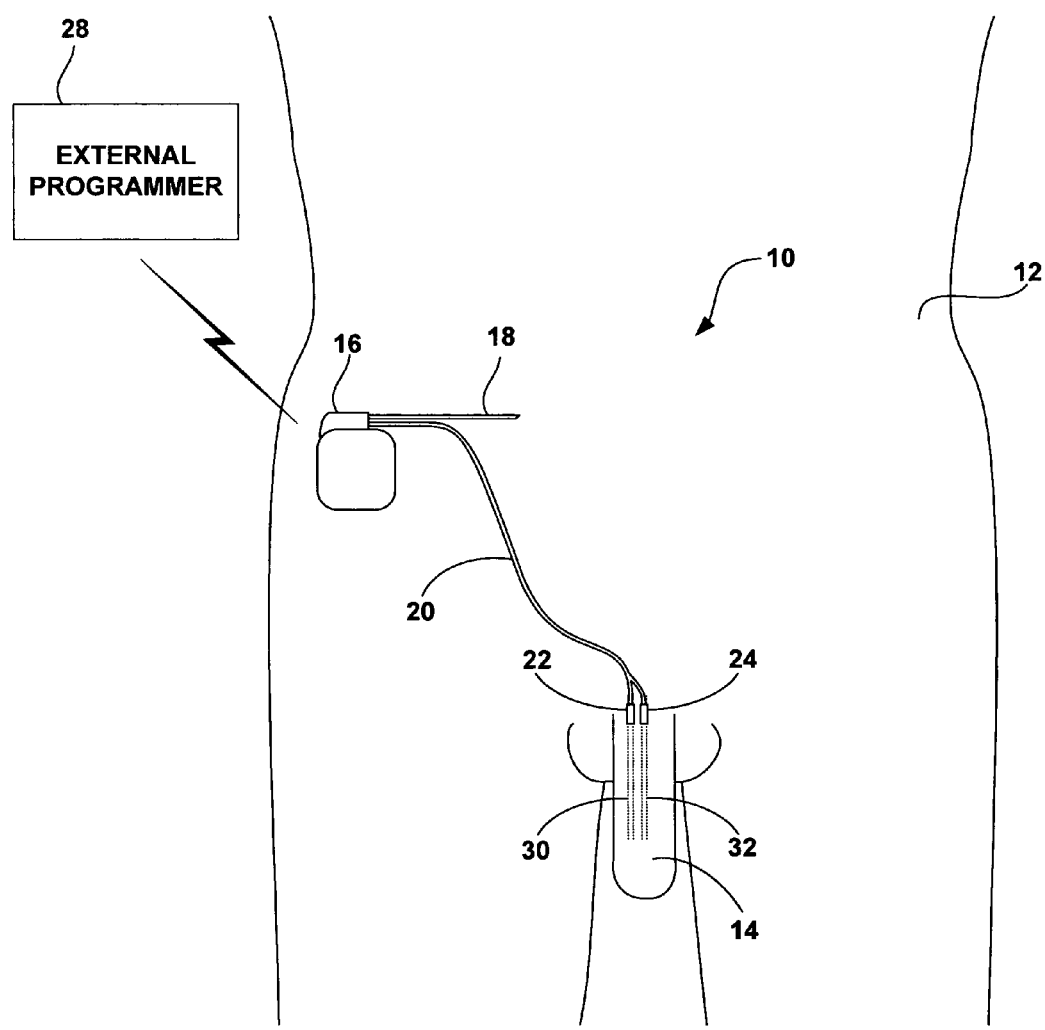
FIG. 1 is a schematic diagram illustrating an example system for alleviation of erectile dysfunction, the system including two wired flow sensors.

FIG. 1 is a schematic diagram illustrating an example system 10 for detecting tumescence of an erectile tissue of a patient 12 that incorporates two wired flow sensors. One of the flow sensors detects an arterial flow to the erectile tissue, e.g., the penis in the illustrated example, while the other flow sensor detects a venous flow away from the erectile tissue. The system may generate tumescence information that reflects the state or degree of tumescence of the erectile tissue based on the detected flows. Such information may be stored for short- or long-term monitoring of tumescence, or used as feedback to control delivery of a therapy for treating sexual dysfunction.

Although illustrated herein primarily in the context of a male patient 12 that has a penis 14 as erectile tissue, systems according to the invention may be provided to both male and female patients 12. For example, in some embodiments, flow sensors may be implanted in or near the clitoris or other erectile tissue, e.g., tissue that engorges, of the female sexual organs, for detecting the tumescence of such tissues.

In the example embodiment shown in FIG. 1, system 10 includes an implantable medical device (IMD) 16, a first flow sensor 22, a second flow sensor 24 and an external programmer 28. A sensing lead 20 couples IMD 16 to first flow sensor 22 and second flow sensor 24. IMD 16 sends a detection signal to each of the first sensor 22 and second sensor 24, and stimulator 16 receives a signal from each sensor, via lead 20. The received signals are representative of the blood flow through an artery 30 and vein 32, which respectively supply blood to and carry blood away from penis 14.

In the illustrated example, first flow sensor 22 is located adjacent to artery 30, which is the deep artery of the penis or profunda penis. Artery 30 supplies blood to erectile tissue called the corpus cavernosum. After blood flows from artery 30 and through the corpus cavernosum, blood exits penis 14 through vein 32, which is also called the deep dorsal vein. While specific blood vessels are described for the purposes of this exemplary embodiment, it is understood that blood flow through any blood vessels, arteries or veins, may be detected to monitor the tumescence level of penis 14. Sensors 22 and 24 may be implanted within or near penis 14, as illustrated in FIG. 1.

In some embodiments, system 10 may be used to monitor blood flow in and out of a clitoris or other erectile tissue of the female sexual organs. In some female patients, erectile dysfunction, such as engorgement problems, associated with sexual dysfunction may be monitored and/or treated with systems including tumescence sensors according to the invention. Therefore, the elements of system 10 described herein may be utilized in female patients as well as male patients. It should be noted that the placement of first sensor 22 and second sensor 24 may be different to monitor blood flow to and from female erectile tissue, such as the clitoris.

The arterial and venous flows reflect the degree or state of tumescence of penis 14. IMD 16 generates tumescence information based upon the detected arterial and venous blood flows. Tumescence information may comprise the flows, or may be determined by IMD 16 based on the flows. IMD 16 may generate tumescence information by comparing the arterial and venous flows. For example, tumescence information may comprise the difference or ratio between the flows.

IMD 16 and/or external programmer 28 may monitor the erectile state of penis 14 based on the flows. IMD 16 or programmer 28 may record the tumescence information, e.g., for later presentation to a physician via the programmer or another computing device. Alternatively or additionally, IMD 16 or programmer 28 may use the tumescence information as a feedback to control delivery of a therapy from the IMD to patient 12.

In the illustrated embodiment, IMD 16 delivers electrical stimulation to patient 12 via a lead 18, which may include one or more electrodes as is known in the art. IMD 16 may deliver the stimulation to nerves, e.g., pelvic nerves, associated with the erectile tissue, e.g., penis 12. As examples, IMD 16 may deliver stimulation to one or more of the prostate parasympathetic nerves, the cavernous nerves, the pudendal nerves, or the sacral nerves. In other embodiments, IMD 16 additionally or alternatively delivers one or more therapeutic substances to patient 12 via one or more catheters. Therapeutic substances may include pharmaceutical, chemical or genetic substances. Such substances may be delivered to nerves associated with the erectile tissue or the erectile tissue itself.

In either case, patient 12 may control the therapy delivered by IMD 16 via programmer 28. For example, patient 12 may initiate or terminate delivery of therapy by IMD 16 via programmer 28. Further, IMD 16 or external programmer 28 may control delivery of therapy based on tumescence information by initiating, adjusting, or terminating the therapy based on the tumescence information.

For example, IMD 16 or external programmer 28 may adjust electrical stimulation parameters such as pulse amplitude, rate and width, and electrode polarity or configuration, based on the tumescence information. As another example, IMD 16 or external programmer 28 may adjust the infusion rate, concentration or number of substances delivered to patient 12 based on the tumescence information. For example, erectile function may be effectively controlled through a controlled combination of two delivered drugs the ratio or timing of which may be controlled based on the tumescence information.

In other embodiments, IMD 16 may deliver therapy through mechanisms other than delivery of electrical stimulation or therapeutic substances. For example, therapy may include at least partially restricting venous blood flow from erectile tissue. This restriction may be directed to one or more locations within patient 12, such as restricting blood flow through one or more veins. Restricting blood flow away from erectile tissue may retain blood within penis 14 to control tumescence.

In other embodiments, an IMD may be coupled to a restricting device positioned proximate to a vein. The restricting device may be an inflatable cuff, clamp or other means for at least partially closing a vein such as vein 32. As an example, an inflatable cuff according to the invention may be similar to the cuff disclosed in U.S. Pat. No. 6,319,237, to Krumme, entitled "URINARY SPHINCTER CONTROL DEVICE." As other examples, the restriction device may be similar to those described in U.S. Patent Application Publication No. 2003/0125605 by Forsell, entitled "CONTROLLED IMPOTENCE TREATMENT," U.S. Pat. No. 4,829,990 to Thuroff et al., entitled "IMPLANTABLE HYDROLIC PENILE ERECTOR," or U.S. Pat. No. 4,958,630 to Rosenbluth et al., entitled "METHOD AND APPARATUS FOR TREATING IMPOTENCE."

In such embodiments, the IMD may be implanted as illustrated in FIG. 1, or within the penis proximate to the restriction device. In such embodiments, the IMD may control the restricting device to pressure the outside walls of vein 32 to achieve sensed blood flows corresponding to appropriate tumescence levels. For example, the IMD may activate and deactivate the restriction device when arterial blood flow indicates the onset and end of an erectile event, and control the restriction device during the erectile event to maintain the arterial and/or venous flows at desired levels during the erectile event. In other embodiments, the IMD may activate and deactivate the restriction device in response to patient inputs, e.g., via external programmer 28. While IMD 16 may deliver therapeutic substances to patient 12, or provide venous outflow restriction therapy to the patient, electrical stimulation will be discussed in greater detail herein.

In some embodiments, IMD 16 or programmer 28 may generate adjustments to parameters in response to tumescence information to support delivery of electrical stimulation to support distinct phases of sexual activity, and transition between such phases. For example, based on the tumescence information obtained by IMD 16, the IMD or programmer 28 may adjust stimulation parameters to maintain a particular phase of sexual activity, transition from one phase to another, and transition from one phase to a cessation of sexual activity. Examples of distinct phases of sexual activity include arousal, e.g., desire, erection or lubrication, and orgasm or ejaculation. To support distinct phases of sexual activity and progression between phases, stimulator 16, and programmer 28 may be configured to operate in conjunction with stimulation devices and techniques described in U.S. patent application Ser. No. 10/441,784, to Martin Gerber, filed May 19, 2003, entitled "TREATMENT OF SEXUAL DYSFUNCTION BY NEUROSTIMULATION," the entire content of which is incorporated herein by reference.

Further, in some embodiments, in addition to controlling therapy based on tumescence information, IMD 16 or programmer 28 may control therapy based on input received from the patient. The input that programmer 28 receives from the patient may indicate the degree or intensity of pleasure or other sensations experienced by the patient, or whether the patient is experiencing pain.

The invention is not limited to embodiments that include a therapy-delivering IMD. In some embodiments, an IMD 16 and/or external programmer 28 may store sensed penile tumescence information without delivery of therapy, for short or long-term monitoring of penile tumescence.

Figure 2:
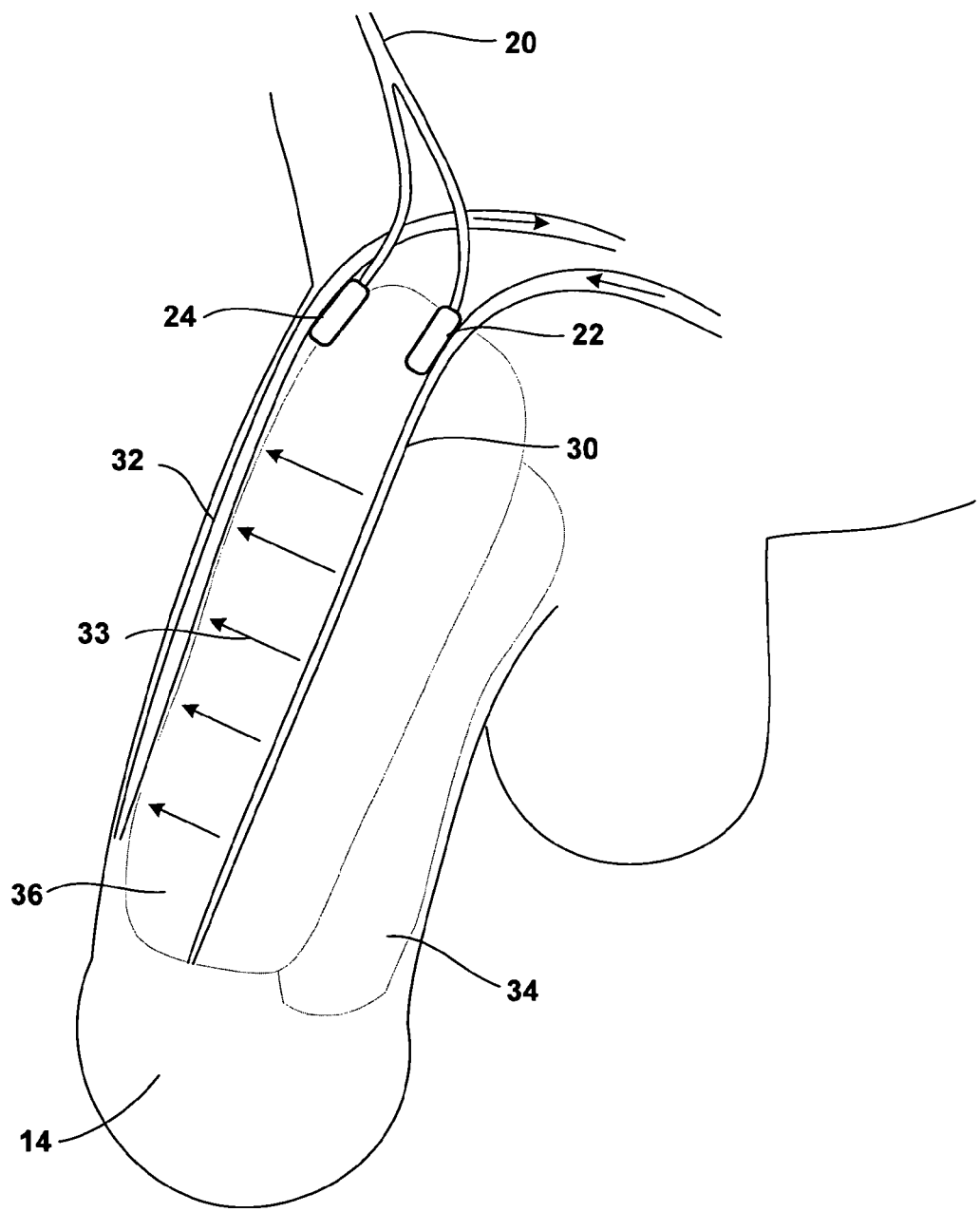
FIG. 2 is an enlarged side view of a penis with two flow sensors each located adjacent a respective blood vessel near the base of the penis for detecting tumescence.

FIG. 2 is an enlarged side view of penis 14 with flow sensors 22 and 24 located adjacent respective blood vessels near the base of the penis for detecting tumescence. First sensor 22 is located adjacent to artery 30 and second sensor 24 is located adjacent to vein 32. In the illustrated example, both sensors 22 and 24 are implanted near the base of penis 14. Artery 30 delivers blood from the heart into erectile tissue 36, blood flows in the direction of arrows 33 through erectile tissue 36, and vein 32 carries blood away from erectile tissue 36. Artery 30 and vein 32 include arrows to indicate the direction of blood flow. Erectile tissue 34 is located on the ventral side of penis 14 and surrounds a urethra. Penis 14 includes an additional erectile tissue (not shown) similar to erectile tissue 36 on the opposite side of erectile tissue 36.

The erectile tissue within penis 14 engorges with blood upon sexual arousal resulting in an erection useful for sexual intercourse. An increase in blood flow to penis 14 allows the penis to swell and become rigid in its erect state. In a physiologically normal patient 12, the parasympathetic nervous system causes arteries, such as artery 30 commonly called the deep artery of the penis or profunda penis, to relax and dilate. The relaxed artery 30 allows more blood to flow through the artery because the diameter of the vessel is larger. An increase in blood from artery 30 fills small blood reservoirs within erectile tissue 36, named the corpus cavernosum. The increasing volume of erectile tissue 36 directs force against vein 32 (the deep dorsal vein), which partially closes the vein. The partially closed vein 32 prevents the increasing volume of blood from leaving erectile tissue 36, thus increasing the tumescence level and causing an erection. Similar mechanisms are responsible to the engorgement of other erectile tissues which engorge simultaneously with erectile tissue 36, such as erectile tissue 34.

The tumescence level decreases when artery 30 constricts blood flow to erectile tissue 36 and blood flow through vein 32 increases. This decrease in tumescence can be caused by a decrease in parasympathetic nerve impulses or an increase in sympathetic nerve impulses. Sympathetic nerve impulses increase due to anxiety or an orgasm, which in turn cause a decrease in tumescence and a loss of an erection. Since increased parasympathetic nervous activity causes and sustains erections, electrical stimulation therapy of these nerves may help to increase and sustain penile tumescence. Monitoring blood flow associated with penis 14 may be an appropriate feedback mechanism to this therapy.

As further shown in FIGS. 1 and 2, first sensor 22 is located on the dorsal side of artery 30 while second sensor 24 is disposed on the ventral side of vein 32. In addition, both sensors 22 and 24 are disposed near the base of penis 14. First sensor 22 may be implanted within erectile tissue 36, and second sensor 24 may be disposed between erectile tissue 36 and vein 32. This placement may be desired so that sensors 22 and 24 do not interfere with normal patient activity or are subject to changing position repetitively with changing tumescence level. However, sensors 22 and 24 may be placed near any blood vessels that service erectile tissue. IMD 16 may employ a calibration method to account for flows in varying sizes of blood vessels. The ability to place sensors at numerous sites may provide flexibility to patients with other conditions or ailments.

Sensing lead 20 may tunnel through the abdomen of patient 12 to couple sensors 22, 24 with IMD 16. In the illustrated embodiment, sensing lead 20 is bifurcated, and coupled to both of sensors 22, 24. In other embodiments, each of the sensors may be coupled at a respective position along a single elongated structure, or the sensors may be coupled to IMD 16 by respective leads.

Sensing lead 20, first sensor 22 and second sensor 24 may be surgically or laparoscopically implanted within patient 12. Sensors 22 and 24 may be placed at respective locations in penis 14, and sensing lead 20 rolled back to leave each component tunneled within tissue. Alternatively, each component may be separately implanted and subsequently connected to sensing lead 20.

Sensors 22, 24 may be Doppler flow sensors. In some embodiments, IMD 16 may send electrical signals to first sensor 22 and second sensor 24 via sensing lead 20, which energize respective transducers within the sensors. The transducers within sensors 22, 24 may produce, for example, ultrasound waves at a certain frequency, which may be emitted at an angle into the respective blood vessel. The transducers may be piezoelectric transducers, or other transducers which can translate electrical energy to mechanical energy or mechanical energy to electrical energy. The waves reflect off of particulates within the blood, such as red blood cells. The reflected waves are of an altered frequency, and are received by the emitting transducers, or other respective transducers within sensors 22, 24. In other words, each of sensors 22, 24 may include one or more transducers. The received waves cause the transducers to produce electrical signals which is sent to IMD 16 via sensing lead 20. IMD 16 may activate each of sensors 22, 24 for a measurement at the same time, or different times.

IMD 16 (FIG. 1) may generate tumescence information that reflects the state or degree of tumescence based on the signals received from sensors 22, 24. For example, IMD 16 may determine the amount of blood flow though vessels 30, 32, which indicates the state or degree of tumescence, based on the signals. In some embodiments, IMD 16 may compare the flows, and a result of the comparison, e.g., a difference or ratio between the flows, may be tumescence information. In some embodiments, IMD 16 may actually determine a state, degree, or percentage of tumescence based on the signals, flows, difference or ratio, e.g., using a look-up table, function or the like.

In some embodiments, IMD 16 may transmit the signals from sensors 22, 24 to external programmer 28, which may generate tumescence information based on the signals in the manner described above. In other embodiments, IMD 16 may generate tumescence information, as described above, and transmit the tumescence information to external programmer 28. IMD 16 or external programmer 28 may store the tumescence information for short- or long-term monitoring of tumescence. The tumescence information may be presented to a user via external programmer 28 or another computing device.

Additionally or alternatively, IMD 16 or external programmer 28 may control delivery of therapy by the IMD based on the tumescence information. The IMD or programmer may initiate, modify, or terminate the therapy based on the tumescence information. In some embodiments, the level of therapy may be modified based on closed-loop feedback from first sensor 22 and second sensor 24 to maintain the tumescence of penis 14 at a target level. In this manner, IMD 16 may deliver therapy in order to achieve and maintain desired tumescence.

In some embodiments, IMD 16 may be coupled to a stimulation lead 18 carrying one or more electrodes that are placed at a nerve site within the pelvic floor. For example, the electrodes may be positioned to stimulate the prostate parasympathetic nerve, the cavernous nerve, the pudendal nerve, or the sacral nerves to support and maintain engorgement of erectile tissue, e.g., an erection of penis 14. In particular, electrical stimulation may be applied to erectile tissue tumescence, e.g., blood flow into penis 14 that enables the patient to achieve an erection and participate in normal sexual activity.

At predetermined times IMD 16 or programmer 28 may initiate stimulation, or at patient controlled instances external programmer 28 may direct IMD 16 to begin stimulation to achieve an erection. Upon the completion of sexual activity as indicated by patient 12 via programmer 28, or after a predetermined period of time, IMD 16 or programmer 28 may cease stimulation to allow blood to flow out of erectile tissue and the erection to subside.

During the course of stimulation, IMD 16 may adjust the stimulation delivered to the patient. For example, adjustment of stimulation parameters may be responsive to tumescence information generated based on the flows detected by first sensor 22 and second sensor 24. External programmer 28 or IMD 16 may adjust stimulation parameters, such as amplitude, pulse width, and pulse rate, based on the tumescence information. In this manner, IMD 16 adjusts stimulation to either increase or reduce penile tumescence based on the actual tumescence level detected of penis 14.

Tumescence information is generated based upon the blood flows detected by first sensor 22 and second sensor 24. In some embodiments, the differential flow between the two measurements is monitored. Blood flow measured by first sensor 22 is representative of the amount of blood being delivered to erectile tissue 36, or inflow. Blood flow measured by second sensor 24 is representative of the amount of blood leaving erectile tissue 36, or outflow. In general, when the inflow measurement is greater than the outflow measurement, tumescence is increasing. In general, when the inflow measurement is less than the outflow measurement, tumescence is decreasing. Equal inflow and outflow measurements represent a steady state of the tumescence level. IMD 16 or programmer 28 may compare the inflow and outflow, which may indicate a degree or state of tumescence.

In some embodiments, IMD 16 or programmer 28 may calibrate first sensor 22 and second sensor 24 to normal blood flows within artery 30 and vein 32 outside of tumescence activity. This calibration may be performed on a regular basis, such as daily, to ensure baseline blood flows. Baseline blood flow data may be necessary to accurately detect the tumescence level of penis 14 during an erection. The baseline blood flow levels may also be stored within IMD 16 or programmer 28 for diagnostic purposes.

In other embodiments, more than two flow sensors may be implanted within patient 12. Multiple arterial or venous blood flows may be monitored to generate a more accurate tumescence level of all erectile tissues. In this manner, IMD 16 or the programmer may be able to sample more than two representative blood vessels for monitoring blood flowing into and out of penis 14.

IMD 16 or programmer 28 may sample flow measurements, or the tumescence level, periodically e.g., every few seconds, during the course of sexual activity. Alternatively, each flow measurement may be processed in response to a request from the program within IMD 16 or programmer 28. Programmer 28 may activate IMD 16, e.g., by wireless telemetry, to commence sensing. In some embodiments, IMD 16 or programmer 28 may process tumescence information when there is an abrupt change in tumescence level, e.g., a tumescence level that exceeds a predetermined rate threshold, which indicates sexual arousal. In this case, IMD 16 may sense tumescence levels at relatively long intervals, and then self-activate sensing at shorter intervals upon detection of the onset of sexual activity.

External programmer 28 may be a small, battery-powered, portable device that may accompany the patient 12 throughout the day or only during sexual activity. Programmer 28 may have a simple user interface, such as a button or keypad, and a display or lights. Patient 12 may initiate an erection, i.e., a voluntary increase in penile tumescence, via the user interface. In particular, in response to a command from the patient 12, programmer 28 may activate stimulator 16 to deliver electrical stimulation therapy, or alternatively deactivate IMD when no electrical stimulation therapy is desired. External programmer 28 may also receive input from patient 12 regarding the progress of therapy, which may be used by the programmer or IMD to control adjustment of therapy parameters. For example, patient 12 may signal that more or less tumescence is desired, or patient 12 may provide input via the external programmer that is relayed to IMD 16 relating to perceived pleasure or pain. In some embodiments, the length of time for an erection event may be determined by pressing a button a first time to initiate stimulation and a second time when the sexual activity is complete, or by a predetermined length of time permitted by programmer 28 or implantable stimulator 16. In each case, programmer 28 causes implantable stimulator 16 to temporarily stimulate patient 12 to promote penile tumescence.

IMD 16 may be constructed with a biocompatible housing, such as titanium or stainless steel, and surgically implanted at a site in patient 12 near the pelvis. The implantation site may be a subcutaneous location in the side of the lower abdomen or the side of the lower back. One or more electrical stimulation leads 18 are connected to implantable stimulator 16 and surgically or percutaneously tunneled to place one or more electrodes carried by a distal end of the lead at a desired nerve site, such as a prostate parasympathetic, pudendal, sacral, or cavernous nerve site.

Figure 3:
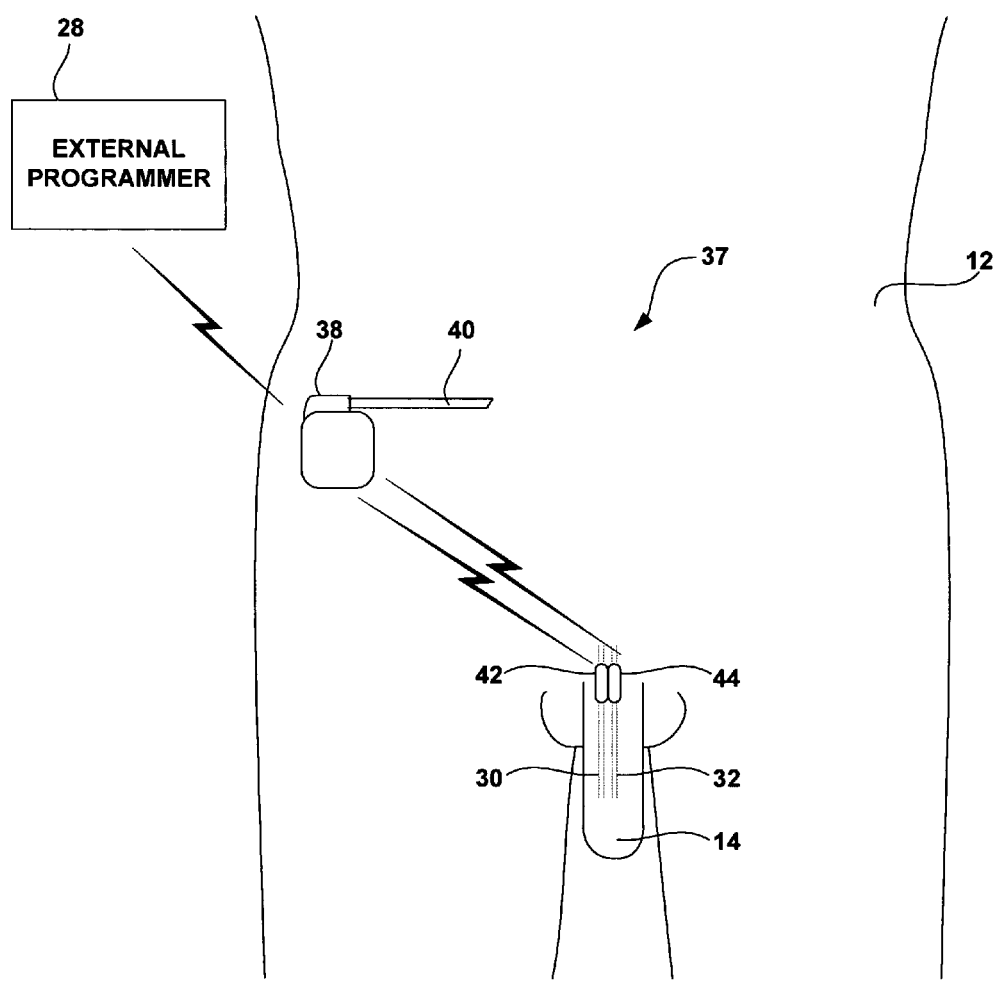
FIG. 3 is a schematic diagram illustrating another example system for alleviation of sexual dysfunction, the system incorporating two wireless flow sensors.

FIG. 3 is a schematic diagram illustrating another example system 37 that senses penile tumescence, the system including two wireless penile tumescence sensors. System 37 includes an IMD 38, a first wireless sensor 42, second wireless sensor 44 and external programmer 28. Each of IMD 38, sensors 42, 44 and external programmer 28 may provide functionality substantially similar to their counterparts 16, 22, 24 and 28 in system 10 discussed above with reference to FIG. 1. As was described with respect to IMD 16 and lead 18 of FIG. 1. IMD 38 delivers electrical stimulation to patient 12 via a lead 40, which may include one or more electrodes as is known in the art.

Like sensors 22 and 24, sensors 42 and 44 may be implanted within or proximate to erectile tissue of patient 12, e.g., within penis 14. In the example illustrated by FIG. 3, sensors 42 and 44 are implanted proximate to artery 30 and vein 32, respectively, like sensors 22 and 24 illustrated in FIG. 1. However, sensors 42 and 44 are not physically connected to an IMD by a lead, like sensors 22 and 24.

IMD 38 and/or external programmer 28 may communicate wirelessly with first wireless sensor 42 and second wireless sensor 44. IMD 38 and/or programmer 28 may receives a signal from each sensor representative of the blood flow through respective artery 30 or vein 32. IMD 38 and/or external programmer 28 may receive the signal upon request or at defined intervals from each sensor. The IMD and/or programmer may generate tumescence information based on the signals and, in some embodiments, control delivery of therapy by the IMD based on the tumescence information, in any of the manners described above with reference to system 10 and FIGS. 1 and 2.

Additionally, one or more of sensors 42, 44, IMD 38 and external programmer 28 may store tumescence information for short or long-term monitoring of penile tumescence. In either case, such penile tumescence information may be presented to a user, such as a physician, via external programmer 28, or another computing device. Further, the invention is not limited to embodiments that include a therapy delivering IMD 38. In some embodiments, the sensor and/or external programmer may store sensed penile tumescence information without delivery of therapy, for short or long-term monitoring of penile tumescence.

Wireless sensors 42, 44 may house respective power sources. In other embodiments, first wireless sensor 42 and second wireless sensor 44 may be coupled to a power source via an electrical lead. The power source may be implanted within patient 12 and provide extended operational time for both sensors.

As previously discussed in FIG. 1, other embodiments of IMD 16 may include delivering therapy through mechanisms other than electrical stimulation. For example, therapy may include at least partially restricting venous blood flow from erectile tissue. This restriction may be directed to one or more locations within patient 12, such as restricting blood flow through more than one vein. Wireless sensors 42 and 44 may be used as feedback control devices to regulate the level of restriction applied to a vein 32.

Figure 4:
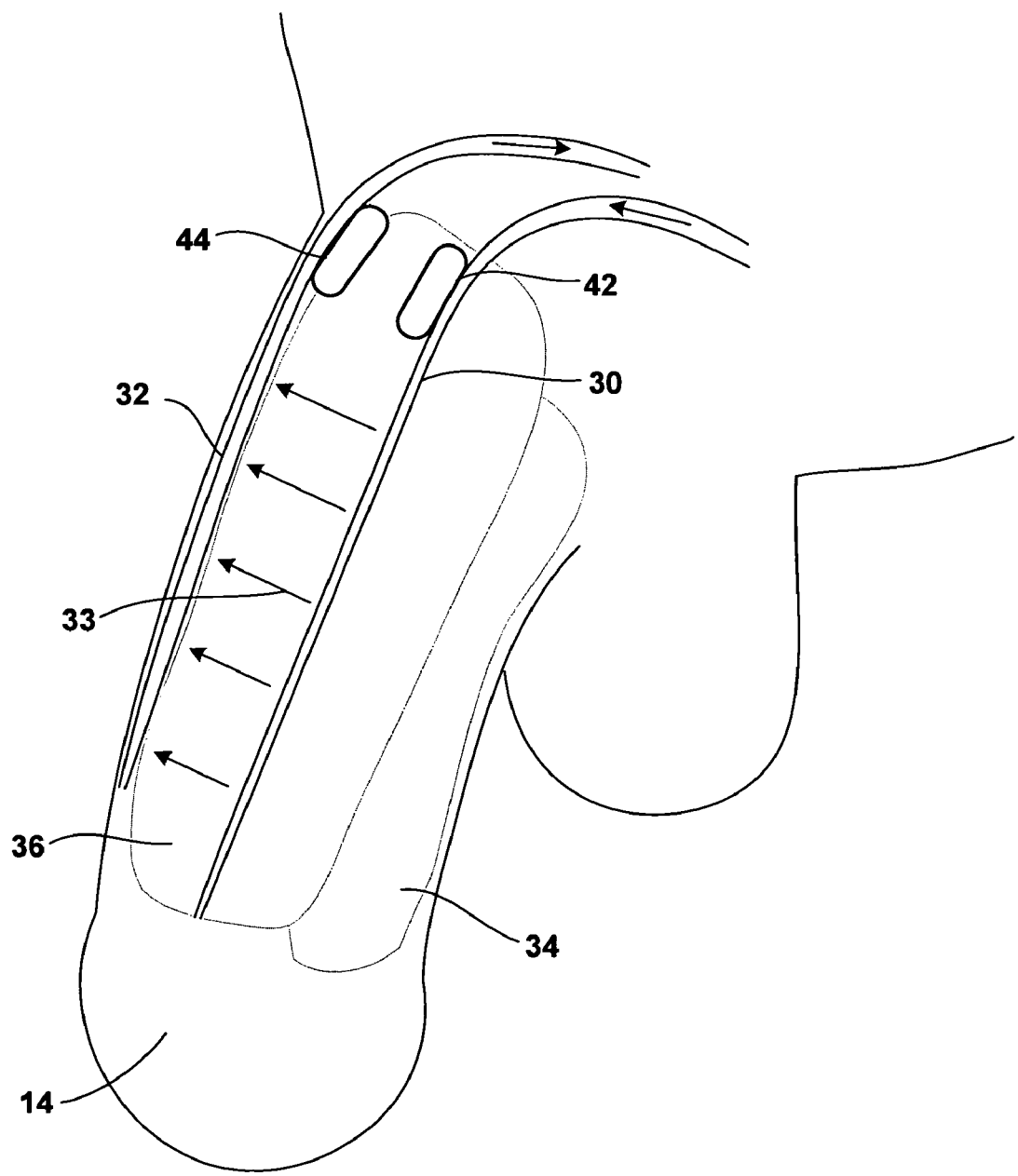
FIG. 4 is an enlarged side view of a penis with two wireless flow sensors each located adjacent a respective blood vessel near the base of the penis for detecting tumescence.

FIG. 4 is an enlarged side view of penis 14 with two wireless sensors 42 and 44 each located adjacent a blood vessel near the base of the penis for detecting tumescence. FIG. 4 shows elements very similar to FIG. 2. As shown in FIG. 4, first wireless sensor 42 is located adjacent to artery 30 and second wireless sensor 44 is located adjacent to vein 32. Both sensors 42 and 44 are implanted near the base of penis 14. Artery 30 delivers blood from the heart into erectile tissue 36, blood flows in the direction of arrows 33 through erectile tissue 36, and vein 32 carries blood away from erectile tissue 36. Artery 30 and vein 32 include arrows to indicate the direction of blood flow. Erectile tissue 34 is located on the ventral side of penis 14 and surrounds a urethra. Penis 14 includes an additional erectile tissue (not shown) similar to erectile tissue 36 on the opposite side of erectile tissue 36.

Either or both of IMD 38 and programmer 28 may wirelessly communicate with sensors 42 and 44, e.g., to activate the sensors for flow measurement and receive signals reflecting the measured blood flows. In some embodiments, one of sensors 42 and 44 may act as an intermediary for wireless communication between the other sensor and the IMD or programmer. Further, one of the IMD and programmer may act as an intermediary for communication between the other of the IMD and the programmer, and the sensors.

First wireless sensor 42 and second wireless sensor 44 may be surgically or laparoscopically implanted within patient 12. Sensors 42 and 44 may be placed at their locations in penis 14 through a catheter or large needle which tunnels to the implantation site. While each sensor may be secure once implanted, sensors 42 and 44 may include a fixation device, such as a hook, barb, screw, helical element, or an expanding hydrogel member. Alternatively, each sensor may be sutured to tissue of or proximate to the blood vessel of interest.

Figure 5:
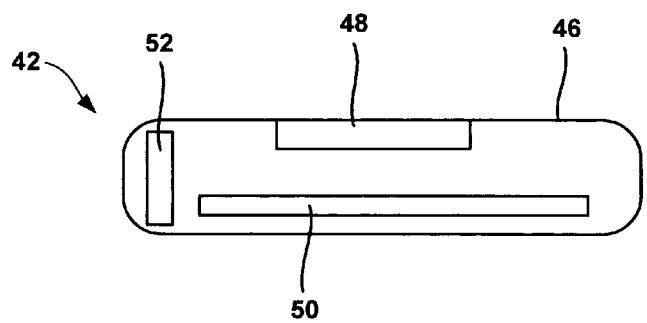
FIG. 5 is an enlarged, cross-sectional side view of a wireless tumescence sensor of FIGS. 3 and 4.

FIG. 5 is an enlarged, cross-sectional side view of the wireless tumescence sensor 42 of FIGS. 3 and 4 according to an example embodiment. Although not depicted in FIG. 5, sensor 44 of FIGS. 3 and 4 may have a substantially similar configuration. The invention is not limited to this example configuration for sensors 42 and 44.

In the illustrated example, sensor 42 includes sensor housing 46, transducer 48, circuit board 50 and power source 52. Sensor housing 46 of implantable sensor 42 may be implanted in the connective tissue or erectile tissue of penis 14. Sensor housing 46 may have a rounded, capsule-like shape, and a smooth, atraumatic surface. Although not shown in FIG. 5, sensor housing 46 may include or be coupled to one or more fixation mechanisms, as described above.

Transducer 48 may send and receive ultrasound waves to detect the blood flow of an adjacent blood vessel, e.g., based on a Doppler shift in the frequency of the ultrasound waves. In other embodiments, sensor 42 may include two or more transducers, each of which may be dedicated either transmitting or receiving ultrasound waves. Transducer 48 is coupled to circuit board 50 within implantable sensor 42.

Circuit board 50 may include a processor, circuitry to cause transducer 48 to generate ultrasound waves, e.g., drive the transducer, and circuitry to process signals produced by transducer 48 from the reflected waves, e.g., analog and/or digital filtering and/or amplification circuitry. In addition, circuit board 50 may include telemetry circuitry for wireless telemetry with IMD 38, external programmer 28, or both. The processor may determine flow rates based on the signals received from transducer 48, or may transmit samples of signals received from transducer 48 to one of IMD 38 or programmer 28 for determination of flow rates.

Power source 52 supplies operating power to transducer 48 and circuit board 50. Power source 52 may take the form of a small rechargeable or non-rechargeable battery, which may be configured as a coin cell or pin cell. Different types of batteries or different battery sizes may be used, depending on the requirements of a given application. To promote longevity, power source 52 may be rechargeable via induction or ultrasonic energy transmission, and includes an appropriate circuit for recovering transcutaneously received energy.

For example, power source 52 may include a secondary coil and a rectifier circuit for inductive energy transfer. Power generation or charging electronics may be carried on circuit board 50. In still other embodiments, power source 52 may not include any storage element, and sensor 42 may be fully powered via transcutaneous inductive energy transfer. As a further alternative, IMD 38 or programmer 28 may be configured to apply inductive power to sensor 42 whenever detection is desired. In this case, when inductive power is not applied, sensor 42 is asleep. Upon application of inductive power, sensor 42 wakes up, acquires a sense signal, and transmits the signal to programmer 28 or IMD 38. Accordingly, in such embodiments, IMD 38 or programmer 28 determines the sampling rate of sensor 42 by powering up the sensor at desired intervals.

Sensor 42 may be implanted within a cavity formed within erectile tissue 36 near artery 30 of penis 14. In some embodiments, sensor 42 may reside partially or completely outside of erectile tissue 36 or other erectile tissue. Sensor 42 may have a capsule-like shape, and may have a length of approximately 2 to 10 mm, a width of approximately 2 to 5 mm, and a thickness of approximately 1 to 5 mm. The capsule-like shape may produce a circular cross-section, in which case sensor 42 may have a diameter of approximately 1 to 5 mm, rather than width and height dimensions.

In some embodiments, housing 46 may have a different shape that is compatible with the anatomy of a particular implant site. For example, sensor 42 may be implanted within or proximate tissue that includes a curved surface. In such embodiments, housing 46 may include a curved surface, e.g., may be convex to provide a larger surface area of contact with artery 30. Housing 46 may also be shaped to be less detectable within penis 14. For example, housing 46 may be substantially flat or disc-like to reduce the potential for protrusion beyond the normal surface of penis 14. Housing 46 may be formed of one or more biocompatible materials, such as titanium, stainless steel, epoxy, or polyvinylchloride.

Figure 6:
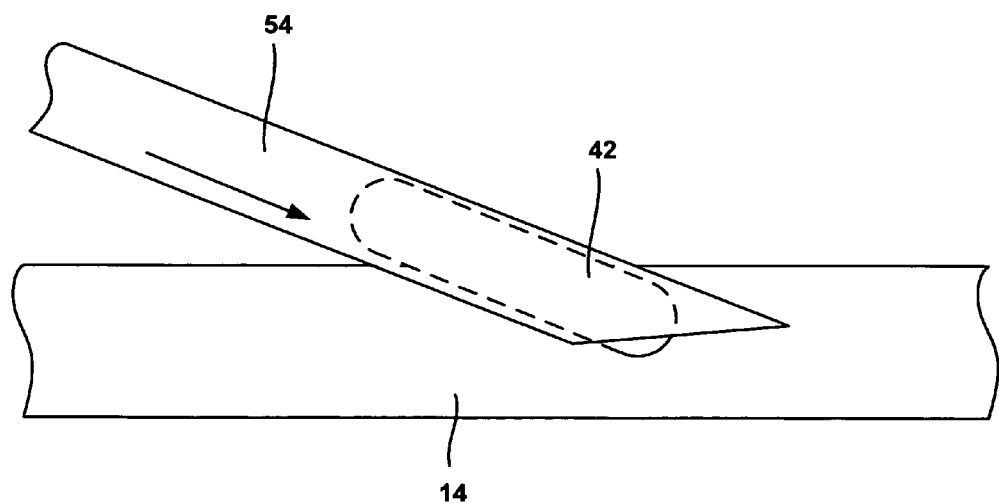
FIG. 6 is a schematic diagram illustrating implantation of a wireless tumescence sensor within erectile tissue.

FIG. 6 is a schematic diagram illustrating implantation of sensor 42 within erectile tissue, e.g., penis 14. Sensor 42 may be implanted using minimally invasive techniques. For example, a surgeon may inject sensor 42 into the connective tissue of penis 14 using a needle 54, as shown in FIG. 6. Needle 54 is constructed of a metal alloy and comprises a hollow cylinder and a pointed distal end for puncturing the skin of penis 14. Needle 54 includes sensor 42, and may include a fluid to force the sensor out of the needle. An exemplary fluid may be saline or other biocompatible fluid. In other embodiments, needle 54 may comprise a catheter or other hollow delivery vehicle.

Once needle 54 in positioned at the appropriate location of penis 14, the surgeon may force sensor 42 into place. Removing needle 54 from penis 14 allows the connective tissue close and surround, or partially surround, sensor 42. In some embodiments, the surgeon may suture the insertion hole to promote tissue healing. The suture may comprise resorbable or non-resorbable suture or staples. Alternatively, a type of synthetic or biological adhesive such as a tissue glue may be used to close the insertion hole. Unnecessary openings within corpus cavernosum 30 or 32 may be avoided to prevent blood loss during tumescence events, infection or other health problems. In other embodiments, sensor 42 may be implanted through more invasive procedures, such as open cutting open the skin of penis 14 and suturing the entire implantation site.

As discussed above, in some embodiments, implantable sensor 42 may carry or include one or more fixation elements that help to anchor the sensor within the connective tissue of penis 14. Such fixation elements may include hooks, barbs, helical elements, tissue ingrowth mechanisms, or hydrogel elements. For embodiments that include hydrogel elements, during implantation, the hydrogel elements are in a dehydrated state, in which the hydrogel elements are smaller. But when implanted in the body of a patient, the hydrogel elements absorb water from the body tissues and assume a larger, hydrated state. One or more expanded hydrogel elements may resist migration of the sensor 42 within penis 14.

Figure 7:
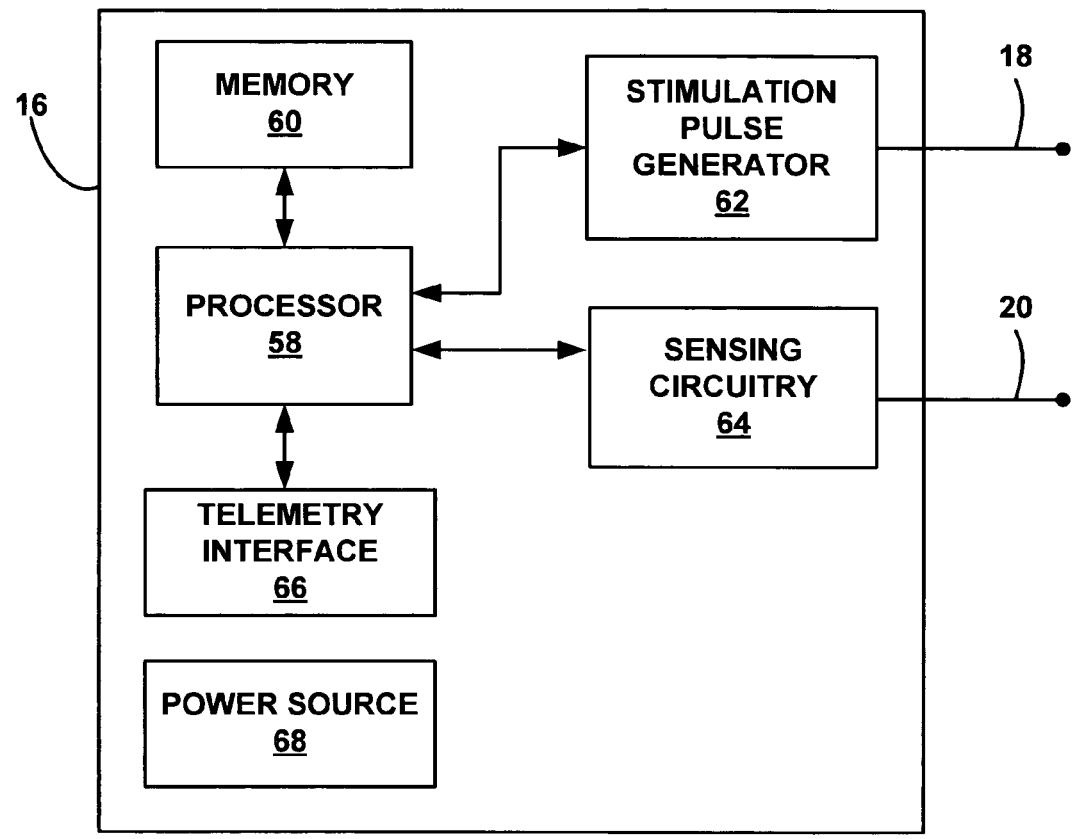
FIG. 7 is a functional block diagram illustrating various components of an example implantable medical device that may be coupled to wired flow sensors, as illustrated in FIGS. 1 and 2.

FIG. 7 is a functional block diagram illustrating various components of IMD 16 of system 10 (shown in FIG. 1) according to an example embodiment. In the example illustrated by FIG. 7, IMD 16 includes a processor 58, memory 60, stimulation pulse generator 62, sensing circuitry 64, telemetry interface 66, and power source 68. Memory 60 may store program instructions for execution by processor 58, which, when executed by processor 58, cause IMD 16 and processor 58 to perform the function ascribed to them herein. Memory 60 may also store stimulation therapy data, e.g., therapy parameters such as pulse amplitude, rate and width. Memory 60 may also store look-up tables, functions, thresholds, or the like, which processor 58 may use to control therapy based on tumescence information generated by processor 58, e.g., based on signals received from sensors 22, 24, or flows, flow differences, or flow ratios derived from the signals. Memory 60 may also store such tumescence information for long or short-term monitoring of penile tumescence. Memory 60 may include any one or more of RAM, ROM, EEPROM, flash memory or the like. Processor 58 may include any one or more of a microprocessor, DSP, ASIC, FPGA, or other digital logic circuitry.

Processor 58 controls sensing circuitry 64 to send electrical signals to first sensor 22 and second sensor 24 via sensing lead 20. The electrical signals drive a transducer in each sensor to emit ultrasonic waves into the blood of the adjacent artery 30 and vein 32. Reflected waves are received by the same or different transducer which translates the reflected wave energy into an electrical flow signal. The electrical signal is sent back through sensing lead 20 to sensing circuitry 64 for processing. Sensing circuitry 64 may include signal generation circuitry known in the art for driving the transducers in sensors 22, 24, as well as analog and digital signal processing circuitry, e.g., filters, amplifiers, or analog-to-digital converters, for processing the electrical signals returned by the sensors. Processor 58 generates tumescence information based upon the signals received from both first sensor 22 and second sensor 24. In other embodiments, processor 58 transmits samples of the signals to programmer 28 via telemetry interface 66, and a processor of the programmer generates tumescence information based on the samples. Tumescence information may include the signals received from sensors 22, 24, or flows, flow differences, or flow ratios derived from the signals.

Sensing circuitry 64 may send electric signals to resonate the transducers to produce ultrasonic waves within a certain frequency. Generally, the frequency of delivered waves may be between 3 MHz and 50 MHz. Preferably, frequencies between 7 MHz and 12 MHz may be used in determining the blood flow within the blood vessels. Reflected waves detected by a transducer may be frequency-shifted based on the rate of flow of blood.

Processor 58 controls stimulation pulse generator 62 to deliver electrical stimulation therapy via one or more leads 18 based on the tumescence information derived from the signals received from sensors 22, 24. For example, processor 58 may determine whether to initiate, terminate or adjust therapy based on the tumescence information. Processor 58 may compare such information to one or more thresholds, look-up tables, or the like, and determine whether to initiate, terminate or modify delivery of therapy based on the comparison. In this manner, processor 58 may directly control therapy in response to information received from sensing circuitry 64. Alternatively, programmer 28 may receive tumescence information from processor 58 via telemetry interface 66, and provide commands controlling therapy parameter adjustments to processor 58 via the telemetry interface.

As an example, if the tumescence information indicates an inadequate tumescence level during a desired erectile event, processor 58 may increase the amplitude, pulse width or pulse rate of the electrical stimulation applied by stimulation pulse generator 62, or change electrode combination or polarity, to increase stimulation intensity, and thereby increase penile tumescence. If tumescence is adequate, processor 58 may implement a cycle of downward adjustments in stimulation intensity until the tumescence level becomes inadequate, and then incrementally increase the stimulation upward until tumescence is again adequate. In this way, processor 58 converges toward an optimum level of stimulation. Although processor 58 is generally described in this example as adjusting stimulation parameters, it is noted that the adjustments may be generated by external programmer 28, as mentioned above.

In some embodiments, IMD 16 may additionally provide an evaluation algorithm in which processor 58 sequentially adjusts the therapy parameters, e.g., according to a lookup table or set of equations stored within memory 60, to identify a parameter combination that is "best" in terms of tumescence or other factors. For example, processor 58 may systematically try to find the set of amplitude, frequency, pulse width and waveform that provides the greatest tumescence for patient 12, as indicated by the flows reflected by the signals received from flow sensors implanted within the patient's penis. Once the best set of parameters has been discovered, processor 58 may store the parameters in memory 60 for later use and exit the evaluation algorithm. The evaluation algorithm may be revisited at any time as requested by patient 12, a physician, or processor 58.

During adjustment of stimulation parameters based on tumescence information, e.g., during feedback operation, or execution of an evaluation algorithm, patient 12 may provide real-time feedback via programmer 28. During execution of the evaluation algorithm, such feedback may be used with tumescence information to score a particular parameter set. Such feedback may indicate, as examples, the degree of sensation or pleasure, or the degree of discomfort or pain, experienced by patient 12 during stimulation with a particular parameter set. During feedback operation, processor 58 may adjust therapy based on tumescence information, as described above, and also based upon such patient feedback. For example, patient 12 may provide feedback relating to the degree of sensation or pleasure, and processor 58 may adjust therapy based on the tumescence information and the indicated degree of sensation or pleasure. Further, if patient 12 experiences discomfort or pain during delivery of, patient 12 may use programmer 28 to indicate the degree of pain, which processor 58 may consider with tumescence information and, in some embodiments, degree of sensation, to control delivery of therapy, e.g., adjustment of parameters.

During feedback operation or execution of an evaluation program, patient 12 may use programmer 28 to direct processor 58 to instantly stop all stimulation, e.g., based on pain experienced by patient. The therapy parameter values currently active when such an event occurs may be stored as "blacklisted" values, e.g., to be avoided, or threshold values which should not be traversed during adjustment of the therapy parameters. As an additional safety mechanism, processor 58 or programmer 28 may compare the current stimulation time to a maximum therapy duration as predetermined by the physician or patient 12. Processor 58 may stop stimulation if therapy has continued for a duration longer than allowed.

As discussed above, in some embodiments, processor 58 may control stimulation pulse generator 62 to deliver stimulation pulses with different parameters for different phases of sexual activity, such as arousal and ejaculation. For a first phase of arousal, processor 58 may control stimulation pulse generator 62 to deliver stimulation pulses at a frequency in the range of generally 10 to 500 Hz, more approximately 50 to 150 Hz, and more preferably approximately 70 to 100 Hz. Each pulse for the first phase may have an amplitude in the range of approximately 1 to 10 volts, and more preferably approximately 2 to 5 volts, and a pulse width in the range of approximately 100 to 400 microseconds, and more preferably approximately 200 to 300 microseconds. The duration of the first phase of stimulation may depend on a detected transition to the second phase, which may be indicated by sensed tumescence.

For a second phase of ejaculation, processor 58 may control stimulation pulse generator 62 to deliver stimulation pulses at a frequency in the range of approximately 1 to 5 Hz, or in the range of approximately 25 to 35 Hz. Each pulse for the second phase may have an amplitude in the range of approximately 1 to 10 volts, and more preferably approximately 2 to 5 volts, and a pulse width in the range of approximately 200 to 700 microseconds, and more preferably approximately 400 to 500 microseconds.

Based on tumescence information, which processor 58 generates based on the signals received from sensing circuitry 64, processor 58 may determine whether any therapy parameter adjustments should be made. For example, processor 58 may compare the tumescence information to one or more thresholds, and then take action to adjust stimulation parameters based on the tumescence information. Signals may be received from sensing circuitry 64, and processor 58 may generate tumescence information based on the signals, on a continuous basis, at periodic intervals, or upon request from or external programmer 28.

As an example, if the tumescence information indicates a that blood inflow is less than blood outflow without the approval of patient 12, processor 58 may increase the amplitude, pulse width or pulse rate, or change electrode combination or polarity, of the electrical stimulation applied by stimulation pulse generator 62 to increase stimulation intensity, and thereby increase blood inflow to the penis. If inflow and outflow both stay constant, processor 58 may implement a cycle of downward adjustments in stimulation intensity until tumescence level reduction is evident, and then incrementally increase the stimulation upward until inflow increases again. In this way, processor 58 converges toward an optimum level of stimulation for purposes of patient comfort and power efficiency. Although processor 58 is described as adjusting stimulation parameters, adjustments alternatively may be generated by programmer 28 and transmitted to processor 58 via telemetry interface 66 as parameter or program changes.

Blood flow to penis 14, such as though artery 30, or away from the penis, such as though vein 32, may change due to a variety of factors, such as an activity type or activity level of patient 12. Hence, for a given set of stimulation parameters, the efficacy of stimulation may vary in terms of rate of tumescence increase or decrease, due to changes in the physiological condition of the patient. For this reason, the continuous or periodic availability of tumescence information from sensing circuitry 64 is highly desirable.

With this tumescence information, stimulator 16 is able to respond to changes in penis 14 blood flow with dynamic adjustments in the stimulation parameters delivered to patient 12. In particular, processor 58 is able to adjust parameters in order to increase or decrease blood flow to penis 14. In some cases, the adjustment may be nearly instantaneous.

In general, if tumescence information indicates that penis 14 is decreasing in tumescence for an unknown reason, processor 58 may increase the level of therapy to be delivered to stop or reverse the decreasing tumescence. Conversely, if tumescence information indicates that penis 14 is increasing in tumescence consistently, processor 58 may incrementally reduce stimulation, e.g., to conserve power resources, until the tumescence level reaches a threshold upper limit. Increases or reductions in the level of therapy may include upward or downward adjustments in amplitude (current or voltage), pulse width, or pulse rate of stimulation pulses delivered to patient 12.

Telemetry interface 66 may include at least one antenna and circuitry for radio frequency (RF) communication or proximal inductive interaction of IMD 16 with external programmer 28. Power source 68 of IMD 16 may be constructed somewhat similarly to power source 54. For example, power source 68 may be a rechargeable or non-rechargeable battery, or alternatively take the form of a transcutaneous inductive power interface.

Figure 8:
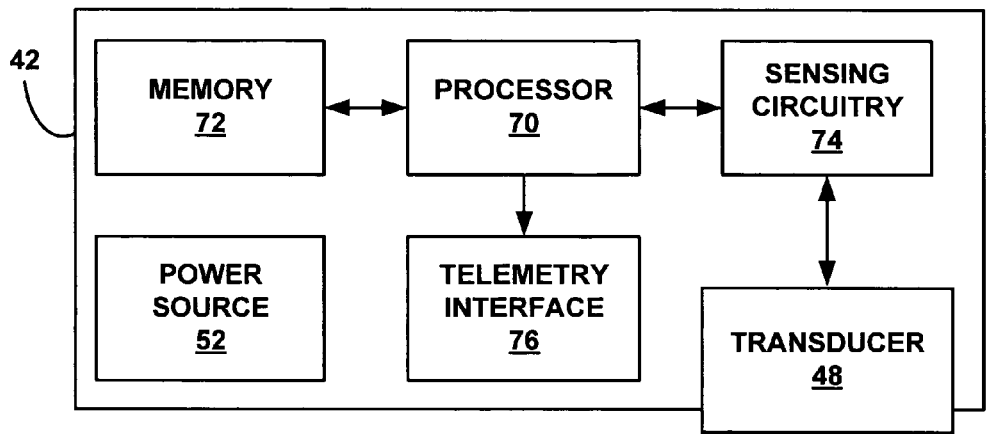
FIG. 8 is functional block diagram illustrating various components of an example wireless tumescence sensor.

FIG. 8 is functional block diagram illustrating various components of an exemplary wireless sensor 42. Although not depicted in FIG. 8, sensor 44 of FIGS. 3 and 4 may have a substantially similar configuration. The invention is not limited to this example configuration for sensors 42 and 44.

In the example of FIG. 8, wireless sensor 42 includes a processor 70, memory 72, sensing circuitry 74, telemetry interface 76, power source 52 and transducer 48. Sensing circuitry 74 may be carried on a circuit board, along with processor 70, memory 72 and telemetry interface 76. Transducer 48 transmits ultrasonic waves into a blood vessel, such as artery 30, to measure blood flow. Transducer 48 also receivers reflected waves from particulates in the blood. These waves have been altered in frequency to represent the velocity of blood flow, known as the Doppler Effect. Transducer 48 modifies the waves into electrical signals that may be amplified, filtered, and otherwise processed as appropriate by sensing circuitry 74 within sensor 42. The signal is reflects the velocity of the blood flow. The signal may be converted to digital values and processed by processor 70 before being saved to memory 72 or sent to IMD 38 or programmer 28 via telemetry interface 76. In some embodiments, transducer 48 may produce the ultrasound waves while another transducer of sensor 42 receives the reflected waves.

Processor 70 may control sensing circuitry 74 to generate electric signals to resonate transducer 48 to produce ultrasonic waves within a certain frequency. Generally, the frequency of delivered waves may be between 3 MHz and 50 MHz. Preferably, frequencies between 7 MHz and 12 MHz may be used in determining the blood flow within a blood vessel. Reflected waves detected by a transducer may be of a frequency determined by the velocity of the flow of blood within the vessel.

Memory 72 stores program instructions for execution by processor 70, and may also stored signals received by sensing circuitry 74. The signals may be sent to implantable IMD 36 or external programmer 28 for generation of tumescence information that may be stored, presented to a user, and/or used to control delivery of therapy to patient 12. In some embodiments, processor 70 of sensor 42 may generate tumescence information based on the signals, and store or transmit the tumescence information. Memory 72 may include any one or more of RAM, ROM, EEPROM, flash memory or the like. Processor 70 may include any one or more of a microprocessor, DSP, ASIC, FPGA, or other digital logic circuitry.

Processor 70 may control telemetry interface 76 to send signals or tumescence information to IMD 36 or programmer 28 on a continuous basis, at periodic intervals, or upon request from IMD 36 or programmer 28. Telemetry interface 76 may include one or more antennae and circuitry for radio frequency (RF) communication or proximal inductive interaction of sensor 42 with programmer 28.

Power source 52 delivers operating power to the components of sensor 42. As mentioned previously, power source 52 may include a small rechargeable or non-rechargeable battery and a power generation circuit to produce the operating power. Recharging may be accomplished through proximal inductive interaction between an external charger and an inductive charging coil within sensor 42. In some embodiments, power requirements may be small enough to allow sensor 42 to utilize patient motion and implement a kinetic energy-scavenging device to trickle charge a rechargeable battery. In other embodiments, traditional batteries may be used for a limited period of time. As a further alternative, an external inductive power supply could transcutaneously power sensor 42 whenever tumescence measurements are needed or desired.

In some embodiments, sensor 42 may be deployed purely as a diagnostic device to obtain and store penile tumescence measurements over a period of time. In particular, sensor 42 may be used to diagnose a patient's condition in order to determine whether the patient suffers from erectile dysfunction, the degree the dysfunction, and whether electrical stimulation therapy may be effective. In each case, sensor 42 is entirely ambulatory and requires little or no setup by the patient 12. Instead, sensor 42 simply accompanies patient 12 throughout his daily routine. Loop recorder functionality may be especially desirable for monitoring of penile tumescence over an extended period of time. Following implantation of IMD 36, sensor 42 may function as both a diagnostic device and a closed loop feedback device for the IMD.

Figure 9:
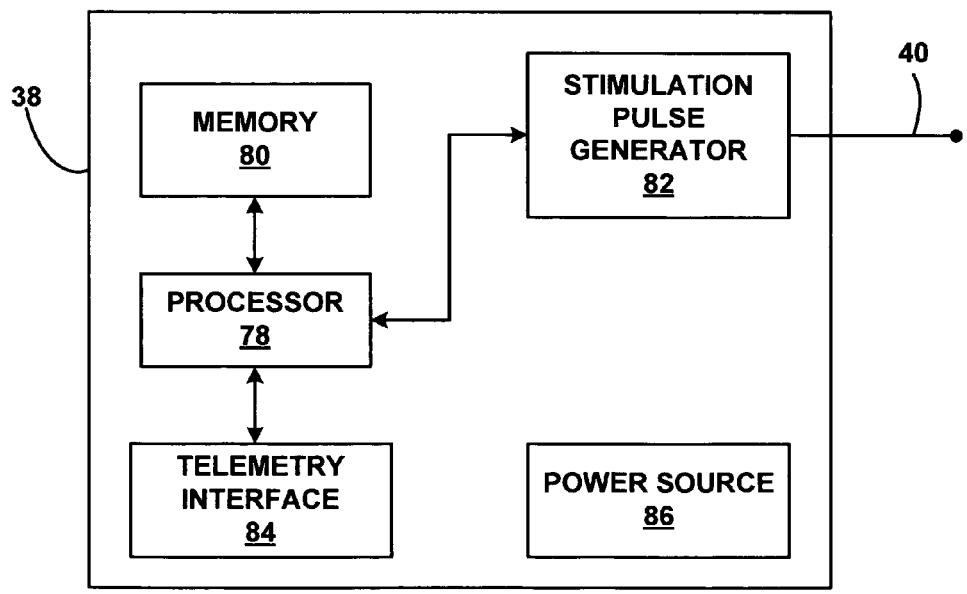
FIG. 9 is a functional block diagram illustrating various components of an example implantable medical device that may be wireless coupled flow sensors, as illustrated in FIGS. 3 and 4.

FIG. 9 is a functional block diagram illustrating various components of an exemplary implantable IMD 38 for use with implantable flow sensors 42 and 44. With the exception of not containing sensing circuitry, IMD 38 is very similar to IMD 16 of FIG. 7. In the example of FIG. 9, IMD 38 includes a processor 78, memory 80, stimulation pulse generator 82, telemetry interface 84 and power source 86, which are substantially similar to the corresponding components of IMD 16 discussed above with reference to FIG. 7. Processor 78 receives tumescence information, or flow signals based upon which processor 78 may generate tumescence information, from sensors 42, 44 via telemetry interface 84. Based on such information, processor 78 may determine whether therapy should be initiated, terminated, or adjusted, as described above, e.g., processor 78 may control stimulation pulse generator 83 to deliver electrical stimulation therapy via one or more leads 40 based on the tumescence information derived from the signals received from sensors 42 and 44. Processor 78 may receive such information from the sensors on a continuous basis, at periodic intervals, or in response to a request made by processor 78 via telemetry interface 84. Alternatively, or additionally, processor 78 may direct sensors 42, 44 to increase the monitoring of tumescence information when there is an abrupt change in the tumescence level, e.g., at the onset of sexual arousal. Processor 78 may control therapy based on tumescence information independently, or, where external programmer 28 receives tumescence information or signals from sensors 42, 44, in response to programming changes from external programmer 28. Processor 78 may provide feedback control of therapy parameters and a therapy parameter evaluation program, as described above with reference to processor 58. Processor 87 may receive feedback from patient 12 via external programmer 28, and use such feedback during closed-loop feedback operation and/or the evaluation program, as described above with reference to processor 58.

Telemetry interface 84 may include antennae and circuitry for radio frequency (RF) communication or proximal inductive interaction with implantable sensor 42 and/or external programmer 28. Also, power source 86 of IMD 36 may be constructed somewhat similarly to power source 54. For example, power source 86 may be a rechargeable or non-rechargeable battery, or alternatively take the form of a transcutaneous inductive power interface.

Figure 10:
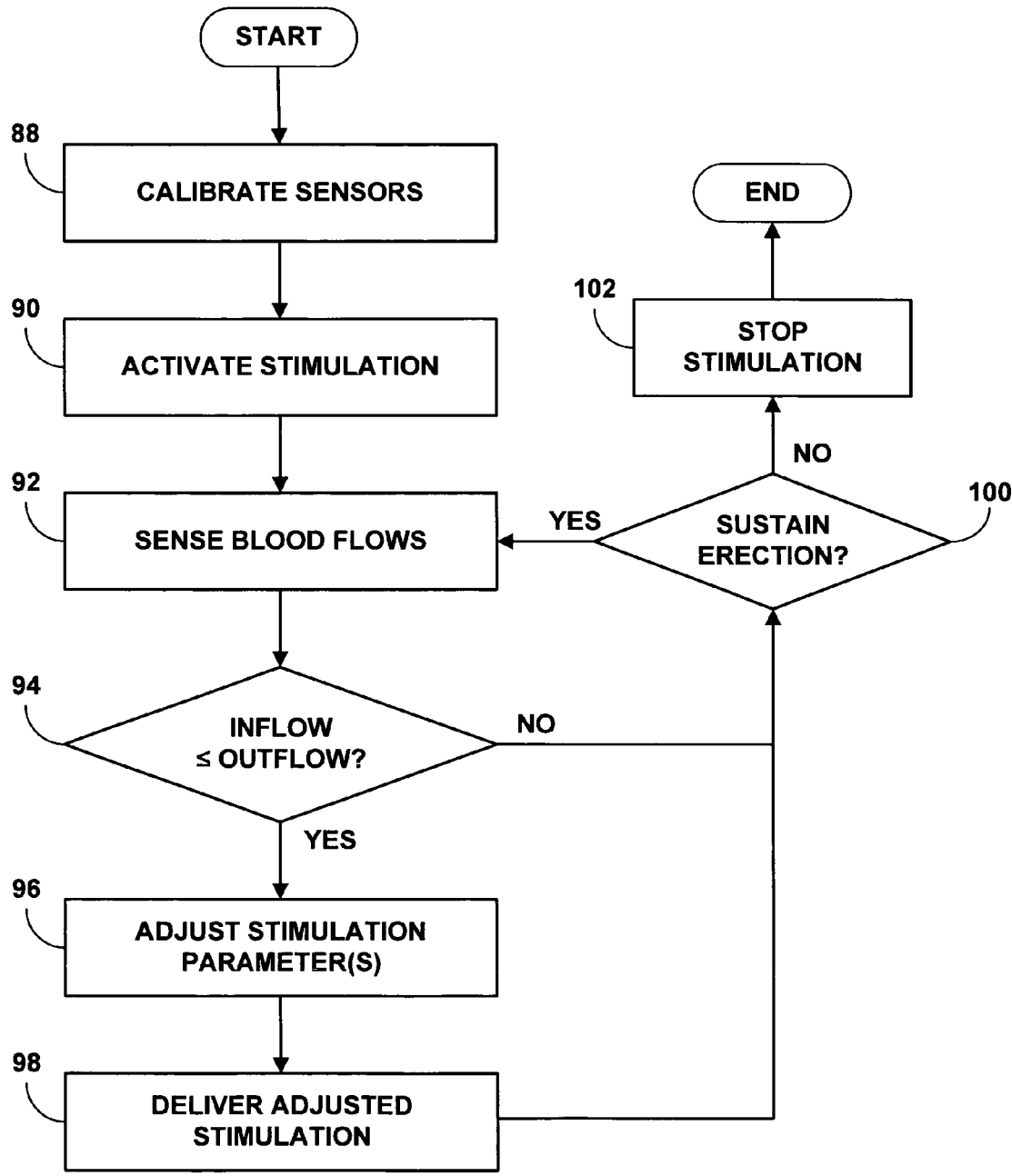
FIG. 10 is a flow chart illustrating a technique for delivery of therapy to alleviate sexual dysfunction based on closed loop feedback from implantable flow sensors.

FIG. 10 is a flow chart illustrating a technique for delivery of stimulation therapy to alleviate sexual dysfunction based on closed loop feedback from implantable flow sensors. In the example of FIG. 10, implantable stimulator 16 makes use of information obtained from first sensor 22, second sensor 24 and external programmer 28. Implantable stimulator 36, first wireless sensor 42 and second wireless sensor 44 may be utilized in this technique in place of their respective wired components.

Before sexual activity, each sensor is calibrated to the baseline blood flow (88). This may be done periodically with normal activity or just before an erection is desired by patient 12. When an erection is desired, patient 12 activates IMD 16 by entering a command via a user interface associated with external programmer 28. The command indicates that the patient would like to commence sexual activity. In response to the command, programmer 28 activates IMD 16 (90) to deliver stimulation therapy.

During the course of stimulation therapy, first sensor 22 and second sensor 24 are utilized by IMD 16 to measure the blood flows associated with penis 14 (92), and IMD 16 or programmer 28 uses the resulting tumescence information, e.g., the signals received from sensors 22, 24, or flows, flow differences, or flow ratios, to control delivery of stimulation. If IMD 16 or programmer 28 determines that the inflow of blood to penis 14 is less than or equal to the outflow from the penis, (94), indicating an inadequate erectile state, the IMD or programmer may adjust one or more stimulation parameters (96) to provide more vigorous stimulation. The adjustment may be made directly by IMD 16 or in response to an adjustment command or reprogramming by programmer 28.

IMD 16 or programmer 28 also determines whether the patient 12 wants to sustain the erection (100), or whether sexual activity has terminated. Patient 12 may terminate sexual activity by entry of a command via a user interface associated with programmer 28 to stop stimulation (102). If sustained erection is desired, the process continues with blood flow measurement (92), flow comparison (94), adjustment of stimulation parameters (96) and delivery of adjusted stimulation (98).

In other embodiments, IMD 16 may continuously cycle stimulation to conserve power. If the inflow is greater than the outflow in block 94, stimulator 16 may slightly decrease stimulation. Adding this step in the processes may help to decrease the operating power required to stimulate patient 12.

Further, as described above, IMD 16, 36 may additionally provide an evaluation algorithm in which the IMD sequentially adjusts the therapy parameters, e.g., according to a lookup table or set of equations stored within a memory, to identify a parameter combination that is "best" in terms of tumescence or other factors. For example, the IMD may systematically try to find the set of amplitude, frequency, pulse width and waveform that provides the greatest tumescence for patient 12, as indicated by the voltage, current or impedance associated with the signal detected by the electrodes implanted within the patient's penis. Once the best set of parameters has been discovered, the IMD may store the parameters for use and exit the evaluation algorithm. In some embodiments, an external programmer 28 may direct the IMD deliver therapy according to a variety of parameters, and may itself evaluate the therapy parameters. The evaluation algorithm may be performed initially in a clinic shortly after implantation of a system as described herein, and revisited at any time as requested by patient 12, a physician, the IMD, or the external programmer.

In some embodiments, as mentioned previously, sensors 22 and 24, or 42 and 44, may be used exclusively for monitoring tumescence without providing feedback for stimulation therapy. For examples sensors 42 and 44 may simply collect flow data for presentation of tumescence information to a user, such as a physician, by programmer 28 or another computing device. In such embodiments, flows may be measured continuously, intermittently or at the request of external programmer 28. These embodiments may be used for, as examples, disease diagnosis or condition monitoring, and may allow a patient to avoid frequent clinic visits and uncomfortable procedures while acquiring more extensive and more accurate tumescence data during sexual activity.

Although the invention has been generally described in conjunction with implantable neurostimulation devices, sensors 22 and 24, or sensors 42 and 44, may also be used with other implantable medical devices, such as implantable drug delivery devices, which may be configured to treat sexual dysfunction. In particular, tumescence information may be used to control delivery of any of a variety of drugs capable of achieving arousal in a male or female patient from a chemical neurostimulation device. Prostaglandin, Alprostdil, Tadalafil, Sildenafil, Vardenfil are examples of drugs that could be infused, e.g., by intracavernous injection, to elicit an erection in a male patient. Approximate dosages for some of the above drugs are: Alprostdil—10 to 250 micrograms, Sildenafil—10 to 250 micrograms, and Apormorphine—10 to 250 micrograms. The tumescence levels obtained by sensor 12 may be used to trigger drug delivery, control the rate of delivery of the drug, or control the overall amount of drug delivered to the patient, e.g., to achieve and maintain an erection during a first phase of sexual activity. A suitable drug delivery system is described in the aforementioned pending application to Gerber.

Various embodiments of the described invention may include processors that are realized by microprocessors, Application-Specific Integrated Circuits (ASIC), Field-Programmable Gate Array (FPGA), or other equivalent integrated or discrete logic circuitry. The processor may also utilize several different types of storage methods to hold computer-readable instructions for the device operation and data storage. These memory or storage media may include a type of hard disk, random access memory (RAM), or flash memory, e.g. Compact Flash or Smart Media. Each storage option may be chosen depending on the embodiment of the invention. While the implantable stimulator and implantable pressure sensor may contain permanent memory, the patient or clinician programmer may contain a more portable removable memory type to enable easy data transfer for offline data analysis.

Many embodiments of the invention have been described. Various modifications may be made without departing from the scope of the claims. These and other embodiments are within the scope of the following claims.

The invention claimed is:
1. A method comprising:
detecting an arterial blood flow to an erectile tissue with a first sensor;
detecting a venous blood flow away from the erectile tissue with a second sensor;
generating tumescence information that reflects the degree of tumescence of the erectile tissue based on the detected arterial and venous blood flows; and
delivering a therapy to a patient to treat sexual dysfunction based on the tumescence information,
wherein generating tumescence information comprises comparing the arterial and venous flows.
2. The method of claim 1, wherein the first sensor and the second sensor are implanted proximate to the erectile tissue.
3. The method of claim 2, wherein the first sensor and the second sensor are implanted within a penis.
4. The method of claim 1, wherein delivering a therapy comprises delivering electrical stimulation.
5. The method of claim 4, wherein delivering electrical stimulation comprises delivering electrical stimulation to at least one of a prostate parasympathetic nerve, a cavernous nerve, a pudendal nerve, or a sacral nerve.

6. The method of claim 1, wherein delivering a therapy comprises at least partially restricting venous blood flow from the erectile tissue at one or more locations.
7. The method of claim 1, wherein delivering a therapy comprises delivering a therapy to at least one of initiate or sustain engorgement of the erectile tissue.
8. The method of claim 1, wherein delivering the therapy comprises delivering the therapy via an implantable medical device.
9. The method of claim 1, further comprising storing tumescence information over a period of time, and presenting the stored tumescence information to a user.
10. The method of claim 9, wherein storing tumescence information comprises storing tumescence information within at least one of a therapy-delivering implantable medical device, an external programmer, or at least one of the first and second sensors.
11. The method of claim 9, wherein presenting the stored tumescence information comprises presenting the stored tumescence information via an external programmer.
12. The method of claim 1, wherein the erectile tissue is located at least partially within a penis or a female sexual organ.
13. The method of claim 1, further comprising:
sequentially delivering therapy according to a plurality of therapy parameter values;
detecting the arterial and venous blood flows via first and second sensors during delivery of therapy according to the plurality of therapy parameter values;
for each of the therapy parameter values, generating tumescence information based on the signals detected during delivery of therapy according to the value; and
selecting a therapy parameter value based on the tumescence information.
14. A system comprising:
a first sensor that detects an arterial blood flow to an erectile tissue;
a second sensor that detects a venous blood flow away from the erectile tissue; and
a processor that generates tumescence information that reflects the degree of tumescence of the erectile tissue based on the detected arterial and venous blood flows, wherein the processor compares the arterial and venous flows, and generates the tumescence information based on the comparison.
15. The system of claim 14, wherein the first sensor and the second sensor each include at least one piezoelectric transducer.
16. The system of claim 14, wherein the first sensor and the second sensor are Doppler sensors.
17. The system of claim 14, wherein the first sensor and the second sensor are implanted proximate to the erectile tissue.
18. The system of claim 17, wherein the first sensor and the second sensor are implanted within a penis.
19. The system of claim 14, further comprising an implantable medical device that delivers a therapy to a patient to treat sexual dysfunction based on the tumescence information.
20. The system of claim 19, wherein the implantable medical device delivers electrical stimulation to the patient to treat sexual dysfunction based on the tumescence information.
21. The system of claim 20, wherein the implantable medical device delivers electrical stimulation to at least one of a prostate parasympathetic nerve, a cavernous nerve, a pudendal nerve, or a sacral nerve.
22. The system of claim 19, wherein the implantable medical device at least partially restricts venous blood flow from the erectile tissue at one or more locations.

23. The system of claim 19, wherein at least one of the first sensor or the second sensor is electrically coupled to the implantable medical device.

24. The system of claim 19, wherein at least one of the first sensor or the second sensor is wirelessly connected to the implantable medical device.

25. The system of claim 19, further comprising an external programmer, wherein at least one of the first sensor or the second sensor is wirelessly connected to the external programmer, and the external programmer controls delivery of therapy by the implantable medical device based on the tumescence information.

26. The system of claim 14, further comprising:
a memory to store the tumescence information over a period of time; and
a user interface to present the stored tumescence information to a user.

27. The system of claim 26, wherein the memory comprises at least one of a memory of a therapy-delivering implantable medical device, a memory of an external programmer, or a memory of at least one of the first and second sensors.

28. The system of claim 26, wherein the user interface comprises a user interface of an external programmer.

29. The system of claim 14, wherein the processor comprises a processor of one of a therapy-delivering implantable medical device, an external programmer, or at least one of the first and second sensors.

30. The system of claim 14, wherein the erectile tissue is located at least partially within a penis or a female sexual organ.

31. The system of claim 14, wherein the first and second sensors are sized for implantation within a sexual organ, and include a power supply and wireless telemetry circuit.

32. The system of claim 31, wherein a housing of at least one of the first and second sensors has a substantially capsule-like shape.

33. The system of claim 14,
wherein the implantable medical device sequentially delivers therapy according to a plurality of therapy parameter values, the first and second flow sensors detecting the arterial and venous blood flows during delivery of therapy according to the plurality of therapy parameter values, and, for each of the therapy parameter values, the processor generates tumescence information based on the signals detected during delivery of therapy according to the value, and
wherein the processor selects a therapy parameter value based on the tumescence information.

34. A system comprising:
means for detecting an arterial blood flow to an erectile tissue;
means for detecting a venous blood flow away from the erectile tissue; and
means for generating tumescence information that reflects the degree of tumescence of the erectile tissue based on the detected arterial and venous blood flows,
wherein the means for generating tumescence information comprises means for comparing the arterial and venous flows.

35. The system of claim 34, wherein the means for detecting an arterial flow and the means for detecting a venous flow are implanted proximate to the erectile tissue.

36. The system of claim 34, further comprising means for delivering a therapy to a patient to treat sexual dysfunction based on the tumescence information.

37. The system of claim 34, wherein the means for delivering a therapy comprises means for delivering electrical stimulation to the patient to treat sexual dysfunction based on the tumescence information.

38. The system of claim 34, further comprising:
means for storing the tumescence information over a period of time; and
means for presenting the stored tumescence information to a user.

39. The method of claim 1, wherein generating tumescence information comprises determining a difference between the arterial and venous flows.

40. The method of claim 1, wherein generating tumescence information comprises determining a ratio between the arterial and venous flows.

41. The system of claim 14, wherein the tumescence information comprises a difference between the arterial and venous flows.

42. The system of claim 14, wherein the tumescence information comprises a ratio between the arterial and venous flows.

43. The system of claim 34, wherein the tumescence information comprises a difference between the arterial and venous flows.

44. The system of claim 34, wherein the tumescence information comprises a ratio between the arterial and venous flows.

45. A method comprising:
detecting an arterial blood flow to an erectile tissue with a first sensor;
detecting a venous blood flow away from the erectile tissue with a second sensor;
generating tumescence information that reflects the degree of tumescence of the erectile tissue based on the detected arterial and venous blood flows; and
presenting the tumescence information to a user via a user interface,
wherein generating tumescence information comprises comparing the arterial and venous flows.

46. The method of claim 45, wherein the first sensor and the second sensor are implanted proximate to the erectile tissue.

47. The method of claim 45, wherein the first sensor and the second sensor are implanted within a penis.

48. The method of claim 45, further comprising delivering a therapy to a patient to treat sexual dysfunction based on the tumescence information.

49. The method of claim 48, wherein delivering a therapy comprises delivering electrical stimulation.

50. The method of claim 49, wherein delivering electrical stimulation comprises delivering electrical stimulation to at least one of a prostate parasympathetic nerve, a cavernous nerve, a pudendal nerve, or a sacral nerve.

51. The method of claim 48, wherein delivering a therapy comprises at least partially restricting venous blood flow from the erectile tissue at one or more locations.

52. The method of claim 48, wherein delivering a therapy comprises delivering a therapy to at least one of initiate or sustain engorgement of the erectile tissue.

53. The method of claim 48, wherein delivering the therapy comprises delivering the therapy via an implantable medical device.

54. The method of claim 45, further comprising storing tumescence information over a period of time, and wherein presenting the tumescence information to the user via the user interface comprises presenting the stored tumescence information to the user via the user interface.

55. The method of claim 54, wherein storing tumescence information comprises storing tumescence information within at least one of a therapy-delivering implantable medical device, an external programmer, or at least one of the first and second sensors.

56. The method of claim 45, wherein presenting the tumescence information to the user via the user interface comprises presenting the tumescence information to the user via an external programmer.

57. The method of claim 45, wherein the erectile tissue is located at least partially within a penis or a female sexual organ.

58. The method of claim 45, further comprising:
sequentially delivering therapy according to a plurality of therapy parameter values;
detecting the arterial and venous blood flows via first and second sensors during delivery of therapy according to the plurality of therapy parameter values;
for each of the therapy parameter values, generating tumescence information based on the signals detected during delivery of therapy according to the value; and
selecting a therapy parameter value based on the tumescence information.

* * * * *